United States Patent
Biggs, Jr. et al.

(10) Patent No.: US 9,149,644 B2
(45) Date of Patent: Oct. 6, 2015

(54) METHOD OF MANUFACTURING A SET SCREW-LESS PACEMAKER HEADER WITH LEAD LOCK SYSTEM

(75) Inventors: James C. Biggs, Jr., Plymouth, MN (US); Thomas F. West, Ramsey, MN (US)

(73) Assignee: Cretex Orthopaedics, Inc., Minneapolis, MN (US)

( * ) Notice: Subject to any disclaimer, the term of this patent is extended or adjusted under 35 U.S.C. 154(b) by 957 days.

(21) Appl. No.: 13/335,297

(22) Filed: Dec. 22, 2011

(65) Prior Publication Data

US 2012/0090161 A1    Apr. 19, 2012

Related U.S. Application Data

(62) Division of application No. 12/260,636, filed on Oct. 29, 2008, now Pat. No. 8,108,045.

(60) Provisional application No. 60/983,483, filed on Oct. 29, 2007.

(51) Int. Cl.
| | |
|---|---|
| *G01R 31/28* | (2006.01) |
| *A61N 1/375* | (2006.01) |
| *H01R 13/52* | (2006.01) |

(52) U.S. Cl.
CPC .......... *A61N 1/3752* (2013.01); *H01R 13/5224* (2013.01); *Y10T 29/49004* (2015.01); *Y10T 29/4998* (2015.01)

(58) Field of Classification Search
CPC . A61N 1/3752; A61N 1/375; A61N 1/37229; A61N 1/362; A61N 1/3627; A61N 1/36521; A61N 1/37; H01R 2201/12; H01R 24/58; Y10T 29/49001; Y10T 29/49128; Y10T 29/49146; Y10T 29/49155; Y10T 29/49169; Y10T 29/49171; Y10T 29/49172; Y10T 29/49176
USPC ................ 29/592.1, 831, 844, 846, 854, 858; 439/909; 607/36, 37
See application file for complete search history.

(56) References Cited

U.S. PATENT DOCUMENTS

| | | | |
|---|---|---|---|
| 4,010,759 A | 3/1977 | Boer | |
| 4,010,760 A | 3/1977 | Kraska et al. | |
| 4,041,956 A | 8/1977 | Purdy et al. | |
| 4,057,068 A | 11/1977 | Comben | |
| 4,182,345 A | 1/1980 | Grose | |
| 4,254,775 A | 3/1981 | Langer | |
| 4,262,673 A | 4/1981 | Kinney et al. | |
| 4,445,511 A | 5/1984 | Cowdery et al. | |
| 4,471,783 A | 9/1984 | Buffet | |

(Continued)

FOREIGN PATENT DOCUMENTS

EP    0006281 A1    1/1980

OTHER PUBLICATIONS

Application and File History for U.S. Appl. No. 12/260,636, filed Oct. 29, 2008. Inventors: James C. Biggs, Jr. et al.

*Primary Examiner* — Paul D Kim
(74) *Attorney, Agent, or Firm* — Patterson Thuente Pedersen P.A.

(57) ABSTRACT

A method for manufacturing a header for an implantable medical device such as a pacemaker which contains an advantageous molded design with encapsulated wires and conductive features. The header including a specifically formed lead lock member in which a plurality of collets residing in bores in the molded housing are used to retain and lock implantable leads in place without the use of set screws.

20 Claims, 11 Drawing Sheets

(56) References Cited

U.S. PATENT DOCUMENTS

| | | |
|---|---|---|
| 4,764,132 A | 8/1988 | Stutz, Jr. |
| 5,070,605 A | 12/1991 | Daglow et al. |
| 5,076,270 A | 12/1991 | Stutz, Jr. |
| 5,086,773 A | 2/1992 | Ware |
| 5,103,818 A | 4/1992 | Maston et al. |
| 5,282,841 A | 2/1994 | Szyszkowski |
| 5,336,246 A | 8/1994 | Dantanarayana |
| 5,489,225 A * | 2/1996 | Julian ............ 439/837 |
| 5,549,653 A | 8/1996 | Stotts et al. |
| 5,643,328 A | 7/1997 | Cooke et al. |
| 5,662,692 A | 9/1997 | Paspa et al. |
| 5,741,313 A | 4/1998 | Davis et al. |
| 5,755,743 A | 5/1998 | Volz et al. |
| 5,871,514 A | 2/1999 | Wiklund et al. |
| 5,919,215 A | 7/1999 | Wiklund et al. |
| 5,951,595 A | 9/1999 | Moberg et al. |
| 5,980,973 A | 11/1999 | Onyekaba et al. |
| 6,026,325 A | 2/2000 | Weinberg et al. |
| 6,052,623 A | 4/2000 | Fenner et al. |
| 6,192,277 B1 | 2/2001 | Lim et al. |
| 6,428,368 B1 | 8/2002 | Hawkins et al. |
| 7,069,081 B2 | 6/2006 | Biggs et al. |
| 7,167,749 B2 | 1/2007 | Biggs et al. |
| 7,650,191 B1 * | 1/2010 | Lim et al. .......... 607/60 |
| 7,751,893 B2 * | 7/2010 | Biggs et al. ........ 607/36 |
| 8,065,009 B2 * | 11/2011 | Biggs ................ 607/37 |
| 8,096,838 B2 * | 1/2012 | Dilmaghanian ...... 439/669 |
| 8,103,348 B1 * | 1/2012 | Coffed et al. ........ 607/37 |
| 2006/0047321 A1 | 3/2006 | Biggs et al. |
| 2009/0192578 A1 | 7/2009 | Biggs |

* cited by examiner

METHOD OF MANUFACTURING A SET SCREW-LESS PACEMAKER HEADER WITH LEAD LOCK SYSTEM

RELATED APPLICATION

This application is a Division of application Ser. No. 12/260,636 filed Oct. 29, 2008, now U.S. Pat. No. 8,108,045, which claims the benefit of U.S. Provisional Application No. 60/983,483 filed Oct. 28, 2007, each of which is hereby fully incorporated herein by reference.

FIELD OF THE INVENTION

The present invention relates generally to medical device header designs and more particularly to implantable medical device header designs with an improved lead locking system which does not require set screws.

BACKGROUND OF THE INVENTION

Pacemakers, cardiac defibrillators, neurostimulators and other implantable medical devices of a variety of shapes, sizes, and configurations have been developed over recent decades. In general, many such implantable medical device designs contain a main hermetically sealed body portion which generates pulses or signals, one or more leads for delivering these transmissions to a desired location, and a header assembly which serves as an intermediary portion for connections between the leads and the main sealed body portion.

In these designs, the main body portion is a sealed member having a housing made of implantable material. Interior components sealed in the main body portion may include a battery, electronic circuits, and other electrical components with only feed-through terminals passing to the outside of the sealed housing for connection with the header.

The leads of these devices are known to vary depending upon their specific desired application. In general, these leads are simply flexible wires coated in insulation that connect a medical device to a location in the body, such as the interior of the heart where wire leads are exposed. For example, leads have been used with a defibrillator and corresponding header for sensing information and delivering stimulation and shock therapy to chambers or appendages of the heart.

Header assemblies typically have been made of plastic or cast epoxy and have been necessary for receiving leads and connecting the leads to the electronic circuitry of the main body portion of a medical device. It is well-known that it is extremely important for leads and wires of an implanted header to avoid contact with fluids or substances which might disrupt or prevent use.

Such headers have typically comprised a small, flat housing compartment made of a plastic casing of partially rounded periphery which integrally fits in a recess adjacent the main body portion of the medical device. Headers also have included openings into which leads may be inserted and retained. Within these openings are contacts for receiving and delivering signals. Often these contacts are welded to conductor wires, contact blocks, and rings by the manufacturer assembling the header and main body of the medical device in a labor intensive procedure. A design which would not require such labor intensive procedure has been sought after in the medical device industry.

Leads placed in the openings of the header housing have almost universally been held in position by one or more set screws. Such set screws were inserted through small holes in the header housing to engage the outer perimeter of the leads from locations on the top or side of the header casing. The seal plug cavities are generally backfilled with silicone, epoxy, or other material in an effort to prevent leaks and avoid unwanted material contact with the screw threads or leads. Unfortunately, these measures have not been entirely effective and significant opportunities for leaks and failures were made possible when using set screws in this manner. A device which eliminates such set screws and passages has long been desired.

In prior designs, seal plug cavities were required to be made according to extremely close tolerances. If not properly made, seal plug cavities often became locations where leak paths were possible. Moreover, bonding septum plugs into the seal plug cavities was required by a user after initial manufacture. This often caused concerns about labor requirements and reliability. There has clearly been a desire to eliminate this difficulties in manufacturing and molding seal plug cavities.

Further, in many prior headers designs, numerous wire channels had to be molded or formed in the outer surface of the header body. Not only was this often a difficult task, but wires placed in such channels had to be backfilled with silicone, epoxy, or other material. This backfilling provided yet another location for potential failures of the connections within the medical device to occur. A header which would improve upon these features which are susceptible to failure has long been desired in the industry.

Therefore, a header for an implantable medical device is desired which provides greater reliability, less labor during and after initial manufacture, the elimination of potential leak paths and enhanced overall safety and performance.

SUMMARY OF THE INVENTION

This embodiment of the invention generally relates to an improved header for a medical device which advances reliability and safety and decreases sources of potential failure. This header includes a polymer housing that is molded to largely encapsulate conductive components within the header. The polymer housing defines a plurality of lead bores molded within the header for receiving leads and an internally threaded anchor member. Each bore includes one or more electrical contacts located around its perimeter which are arranged into place during the molding procedure as well as corresponding wires are coupled to each contact.

The header also includes at least one lead lock member having apertures through which the plurality of lead bores and at least one anchor member are accessed. A fastener passing through the lock member may be adjusted to cause restriction of the lock member within the lead bores. Accordingly, wires passing into the lead bores can be locked in place.

Utilizing these components provides a system which does not require set screws and corresponding passages leading directly to the ends of the leads. The device is therefore able to lock in leads with a nonconductive structure while effectively encapsulating and insulating the header components, including contacts, wires, and leads, from potential failure or interference with operation.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE DRAWINGS

FIGS. 1-27 set forth embodiments of a header design for an implantable medical device such as a pacemaker, cardiac defibrillator, or neurostimulator. The header design disclosed contains a unique lead locking construction by which leads can be effectively retained within bores of the header. The encapsulated header design is particularly advantageous due to its integrally molded features and the ability to eliminate the need for traditional set screws.

Figure 1:
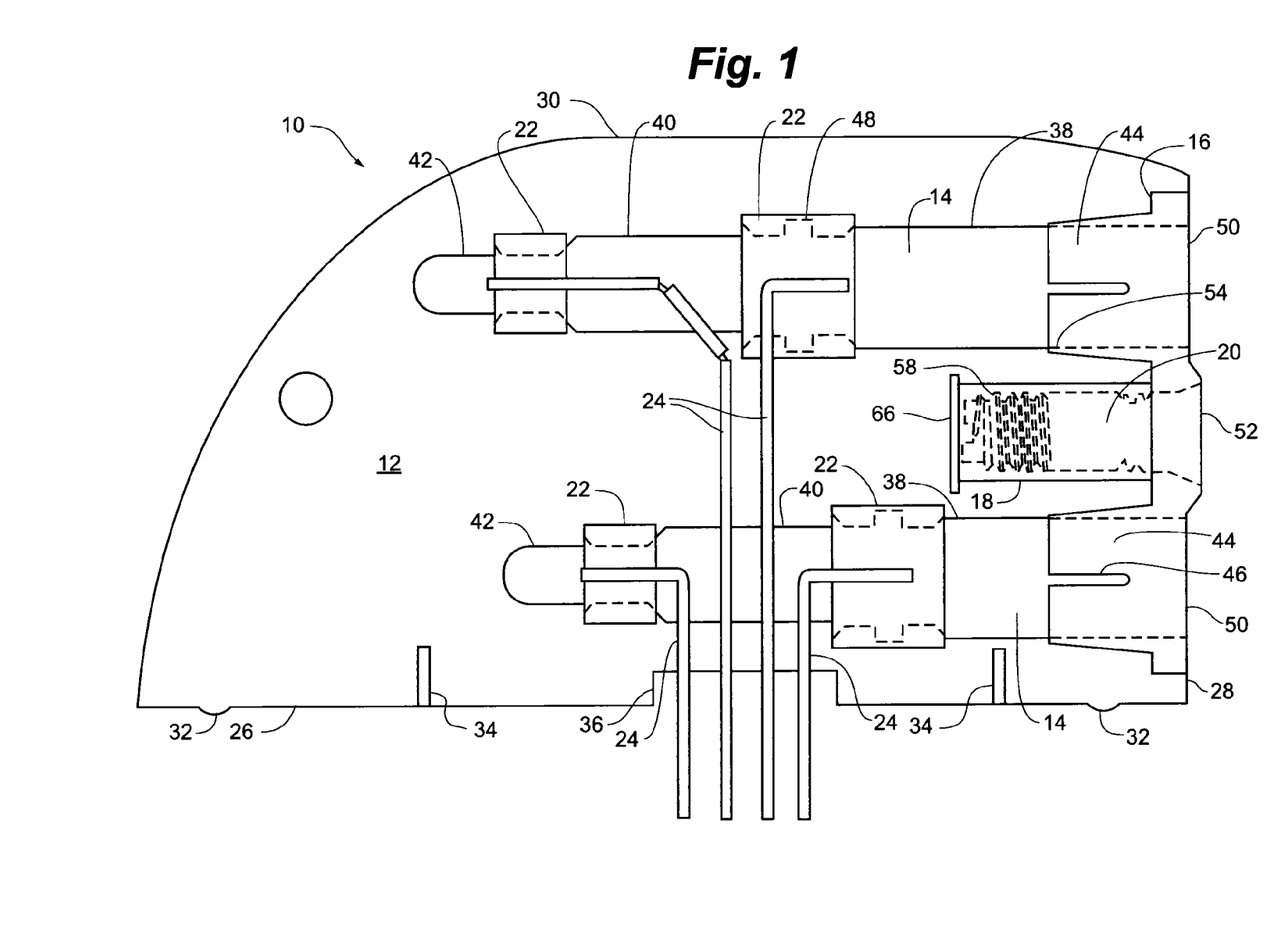
FIG. 1 is a cross-sectional side view of an embodiment of a header of the present invention.
Figures 2, 3:
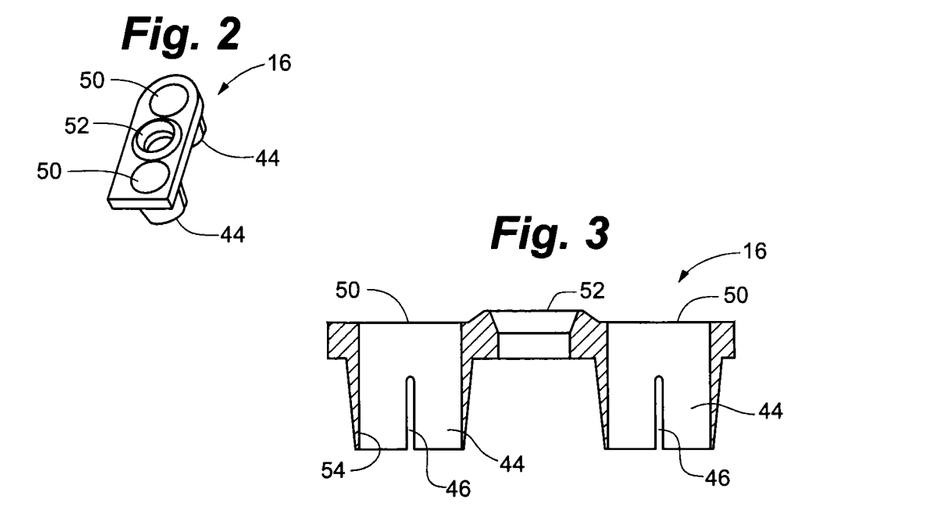
FIG. 2 is a perspective view of the lead lock member of the header of FIG. 1.
FIG. 3 is a cross-sectional view of the lead lock member of the header of FIG. 1.
Figure 4:
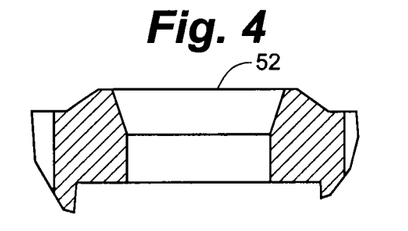
FIG. 4 is a detailed view of the screw hole of the lead lock member of FIG. 3.
Figure 5:
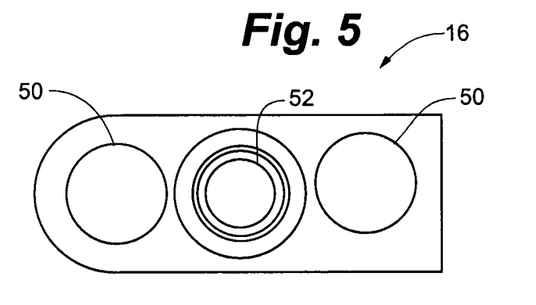
FIG. 5 is an end view of the lead lock member of the header of FIG. 1.
Figure 6:
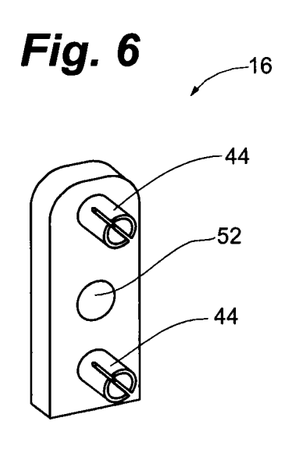
FIG. 6 is an additional perspective view of the lead lock member.
Figure 7:
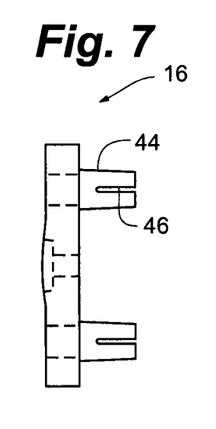
FIG. 7 is a cross-sectional view of the lead lock member.
Figure 8:
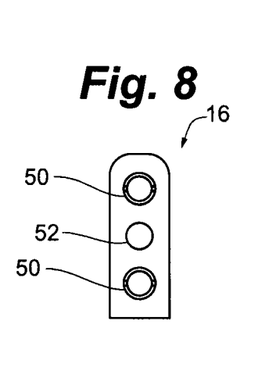
FIG. 8 is an end view of the lead lock member.

In FIG. 1, a cross-sectional side view is shown of an embodiment of the header. The header assembly is generally referred to by numeral 10. The header includes a polymer housing 12 encapsulating most of the features of the header assembly 10 and containing a plurality of lead bores 14, a lead lock member 16, at least one anchor 18 with a fastener 20, and a plurality of contact blocks 22 and header wires 24.

The polymer housing 12 is a small molded member of plastic which is shaped to engage a pacemaker or other medical device. The header housing is relatively narrow in width and has a largely rounded surface shape. The periphery of the device, however, has a lower edge face 26 that is relatively flat and an adjacent side edge face 28 containing a number of formed faces for accommodating a lead lock member 16. The side edge 28 and lower edge 26 are additionally joined by an upper curved edge 30. The header has a smooth outer body without any exposed recessed areas when attached to a medical device. Such smooth outer features allow for enhanced patient comfort after the device is implanted. The housing 12 is compatible with body tissues and can be formed of a variety of well-known biocompatible polymers or other materials which are rigid and can be machined or molded. The polymer housing 12 is created from an extrusion molding process which enables encapsulation of items placed within the mold. Forming the housing in this way creates a structure with components which are electrically insulated from one another and which are rigidly secured into place.

The lower face 26 of the polymer housing 12 has a primarily flat surface for coupling to a receiving feature of an implantable medical device. Lower face 26 does contain a number of small protrusions 32 and bore holes 34 for matching with corresponding protrusions and bore holes on the main body of the implantable medical device to precisely align and mate these components together. A small recessed pocket 36 is also formed into the lower face 26. This pocket 36 provides space in which wires can be welded together between the main device and header 10.

Within polymer housing 12 are two lead bores 14 which extend inward from side face 28 in a stepped, telescoping fashion. The lead bores 14 are shown in FIG. 1 with three axially aligned sections 38, 40 and 42 each having decreasing stepped diameters. These lead bores 14 are shaped to accommodate plugs found at one end of corresponding medical leads. More specifically, these lead bores 14 are formed to accommodate leads shaped according to IS-1, DF-1, and IS-4 standards. Leads of similar shapes and standards may be accommodated as well.

The entry diameter of the lead bores 14 are surrounded by collet members 44 of a lead locking member 16. These collet members 44 are tapered and contain slits 46 in a plurality of locations around their perimeter such that the collet members 44 may be compressed and partially collapsed around an inserted lead when the lead lock member 16 is fastened into place. The lead locking member 16 will later be discussed in greater detail.

The lead bores 14 each are molded with one or more contact blocks 22 surrounding the stepped lead bores 14 in various locations. FIG. 1 shows contact blocks 22 found on the second and third stepped sections 40 and 42 of each lead bore periphery. Some of these contact blocks 22, such as the ones shown in FIG. 1 on the middle stepped section 40, also contain a contact ring 48 to help provide a better accessible source of contact for inserted leads.

Wires 24 are welded to the outside of each of the contact blocks 22 prior to molding the polymer housing 12. Due to the way the polymer housing encases the contact blocks 22 and wires 24, these components need not be secured into place after molding. The wires 24 extend through the inside of the polymer housing 12 until exiting into recessed pocket 36. This recessed pocket 36 is present in the exterior of the housing 12 to provide an area for welding attachment of the header wires 24 to corresponding wire conductors of a main implant body. It is important to note that the wires 24 remain encapsulated in polymer material while passing through the housing 12. This encapsulation insulates the wires from one another and prevents the possibility of leaks around the wires. When the wires 24 are connected to the main body wires in pocket 36, silicone or epoxy is used around these areas to prevent leaks or exposure to harmful materials.

At one end of the polymer housing 12 along side edge 28, is a lead lock member 16 which facilitates locking leads in place. The lead lock member 16 is shown in various views in FIGS. 2-8. Specifically, lead lock member 16 is a multifaced and contoured structure that is joined into the polymer housing 12 along the contoured housing side edge 28. Lead lock member 16 provides integrally shaped openings 50 through which leads can pass into lead bores 14 and includes one or more openings 52 with a counterbore for inserting fasteners 20, such as screws which are aligned with a threaded anchor member 18. The lead lock member 16 also contains features which project from the interior face of the member around the openings 50 referred to as collet members 44. When the lead lock member 16 is joined to the housing 12 the collet members 44 taper inwardly within each lead bore 14 in a frusto-conical fashion. The interior faces 54 of these conical collet member protrusions may be compressed around inserted leads. Additionally, the lead lock member 16 may be shaped, as in FIG. 12, with additional inwardly projecting flanges 56 around the end of the tapered collet members 44. These flanges 56 may be useful for providing an additional structure for constricting collet members 44 around inserted leads.

The lead lock member 16 is integrally shaped to cooperate with one or more screws 20 and corresponding anchor members 18 that have been molded into the polymer housing 12. In FIG. 1, a single anchor 18 is shown at the center of the lead lock member 16. The hollow, internally threaded anchor 18 is molded in place adjacent the edge of the molded polymer material such that the internal threads 58 and features are accessible from outside the molded housing through apertures 52 in the lead lock member 16. A similar lead lock member 60 in which two counterbore screw apertures 62 and 64 could be used with two corresponding anchors is disclosed in FIGS. 13 and 14. In this lead lock design, the counterbored screw apertures 62 and 64 are located above and below the lead bore apertures 50. Despite the structural change, that alternate design would not have a significant operational difference from a single screw design.

In either a single or multi screw configuration, the locking member functions in a similar manner. Both locking members make use of anchor members 18 providing an internally threaded passage into the polymer housing 12. Once leads are inserted into the lead bores 14 one or more screws or fasteners 20 with a tapered head may be screwed through an aperture in the lead lock member into the threaded anchor 18. The lead lock member 16 is integrally shaped such that when the screw 20 is tightened within the anchor 18, the portion of the lead lock member 16 surrounding the screw 20 is compressed and causes the frusto-conically extending collets 44 of the lead lock member 16 to accordingly compress within the corresponding lead bores 14, thereby locking inserted leads in place. In this way, inserted leads may be locked in place using an encapsulated header having a lead lock system that does not require set screws to be screwed into the header assembly in passages adjacent the leads. No backfilling is required of the screw 20 and no passages for leaks to fill are present in this locking process.

Additionally, the anchor 18 used in this design is only partially threaded with threads 58. See FIG. 9. This feature enables the screw 20 to be tightened and loosened along the threaded portion of the anchor 18, yet prevents the screw from completely detaching from the anchor 18. There is no opportunity for a screw to come loose and detach from the header assembly during surgery or otherwise. Therefore, if the leads require removal, a physician may readily turn out the fastener 20. When doing this, the screw turns out only part way and stops turning out when it reaches the interrupted female threaded region 65. No possibility of the entire screw exiting the anchor exists. The lead can accordingly be extracted.

Figure 9:
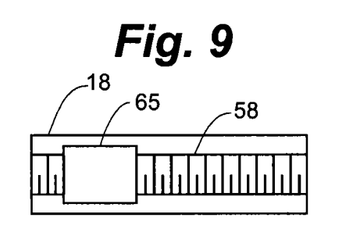
FIG. 9 is a cross-sectional view of the anchor of the header.
Figure 10:
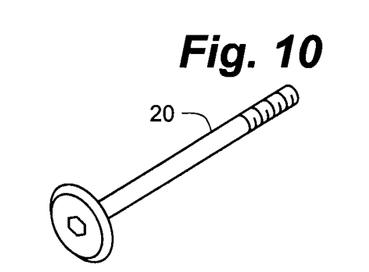
FIG. 10 is a screw fastener for use in the anchor of the header.
Figure 11:
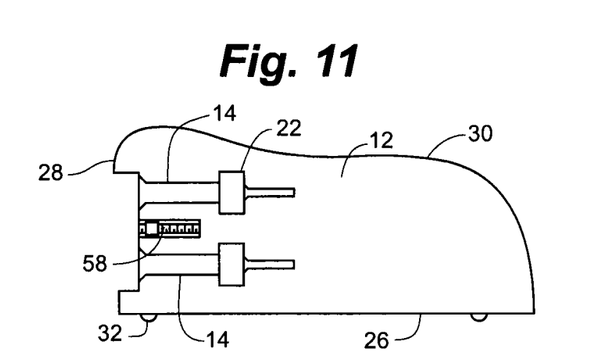
FIG. 11 is a side view of the molded housing of the header.
Figure 12:
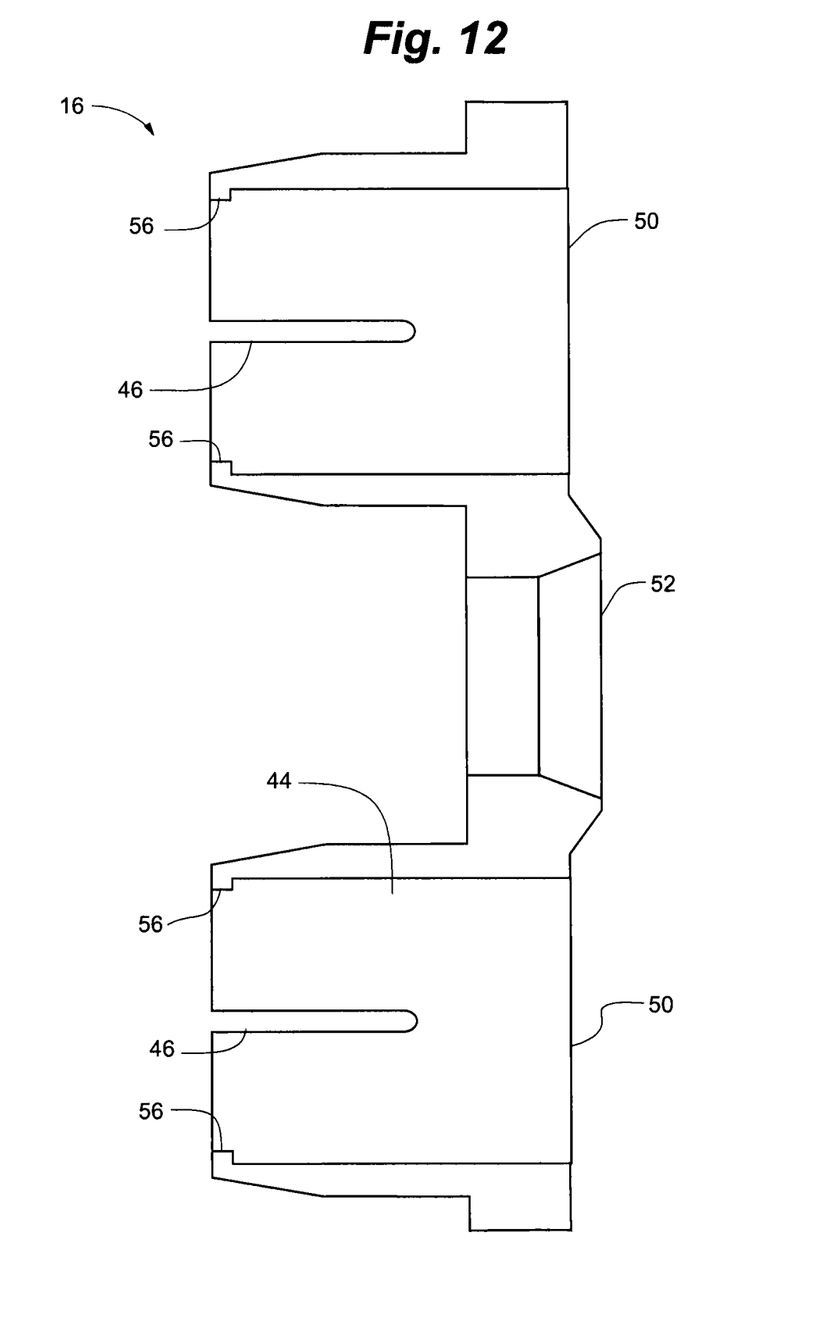
FIG. 12 is a cross-sectional view of an alternative embodiment of the lead lock member of the header.
Figure 13:
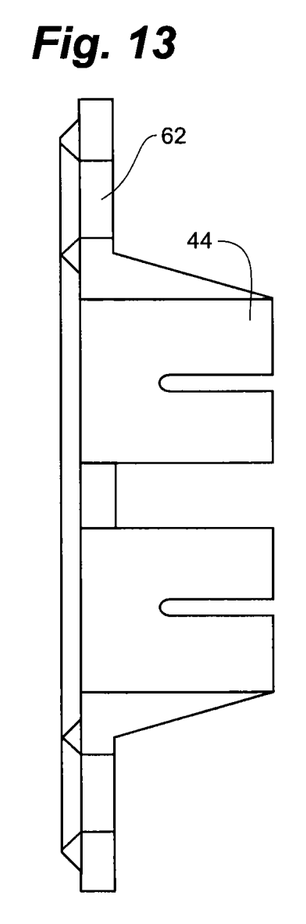
FIG. 13 is a cross-sectional side view of an alternative embodiment of the lead lock member of the header.
Figure 14:
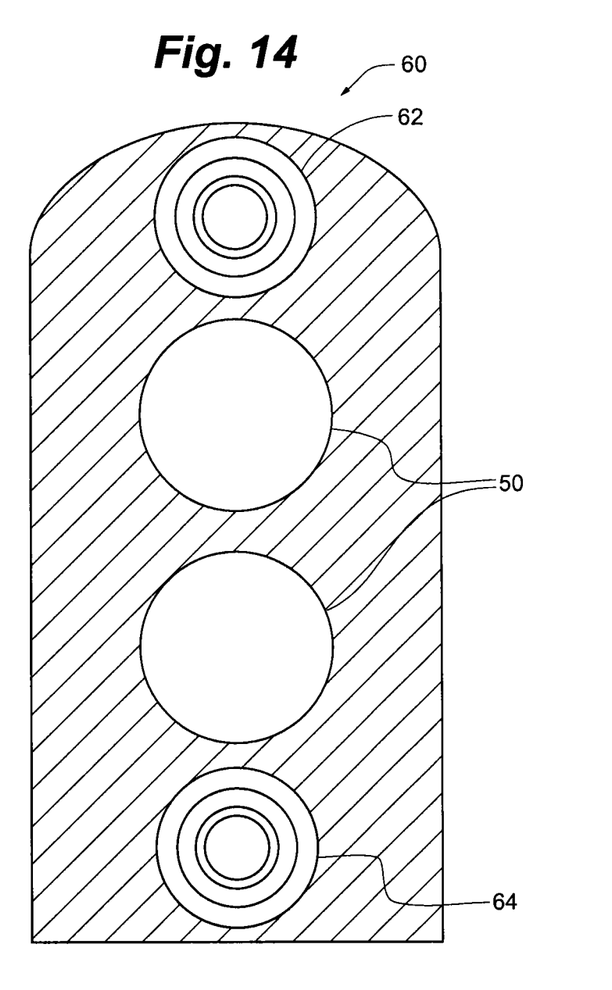
FIG. 14 is an end view of the lead lock member of FIG. 13.

Another important feature of the anchor 18 is the flat flange 66 present at the interiormost end of the anchor 18. This flange 66 is molded into the polymer housing for providing a stable base structure to the anchor 18. Accordingly, anchor screws 20 can be readily tightened or loosened without spinning the anchor 18 or modifying its position.

Therefore, a physician is able to secure leads into the header during surgery with a few simple steps. For example, in a header with a lead lock member 16 having a single screw 20, leads are first inserted into the apertures 50 in the lead lock member so that they reside in the lead bores 14 of the housing 12. Next, the screw 20 found within the counterbore of the lead lock member 16 is tightened.

As the screw 20 is tightened into the mating female anchor 18, the tapered collets 44 of the lead lock member 16 enter into a close tolerance clearance pocket of bores 14. The bores are also tapered around their perimeter to mirror the lead lock collet member 44. The mating tapered configuration allows for a precise fit which eliminates the potential for gaps or openings that would allow fluids to collect. As the screw 20 is threaded into the female anchor 18, the tapered split collet 44, which mates with a mirror image of the same taper angle molded into the lead bore 14, precisely closes down around the lead, locking the lead into position once the desired torque setting on the physician's wrench is reached. Finally, a septum plug (not shown) is used to conceal the head of the screw 20 which is recessed into the counterbore of the lead lock member 16.

Figure 15:
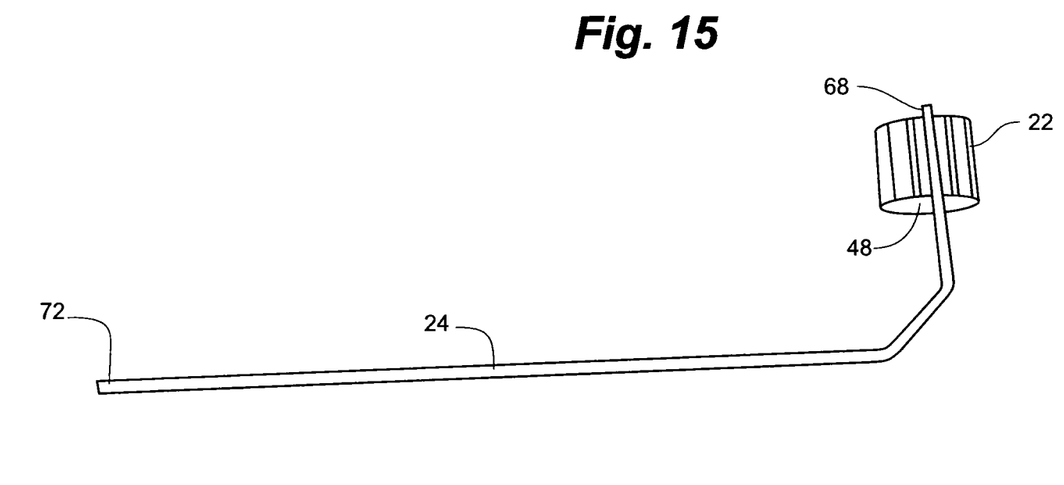
FIG. 15 is a perspective view of a contact ring and a conductor wire.

The manner by which an embodiment of the header of the present invention is constructed allows for retention of components in an advantageous configuration which does not require features like set screws for appropriate attachment. Formation of such a header first requires resistance or laser welding of a first end 68 of a pre-formed wire conductor 24 to a contact block 22 and/or contact ring 48 as seen in FIG. 15. This is done by using high precision positioning tooling to effectively control the exact orientation and geometric position of all sub-assemblies during the plastic injection molding process. The contact blocks 22 and rings 48 are sub-assemblies containing conductive springs or other conductive components that are typically welded into the formed cavity or cross-hole. This configuration enables intimate and robust conductivity between a main lead and the contacts 22 in the molded header. Having such conductivity enables communication to effectively take place between the device and body parts such as the heart. This ensures that the signals from the body or heart to the device can be readily transmitted and responses from the device to the body or heart are recognized instantaneously.

Figure 16:
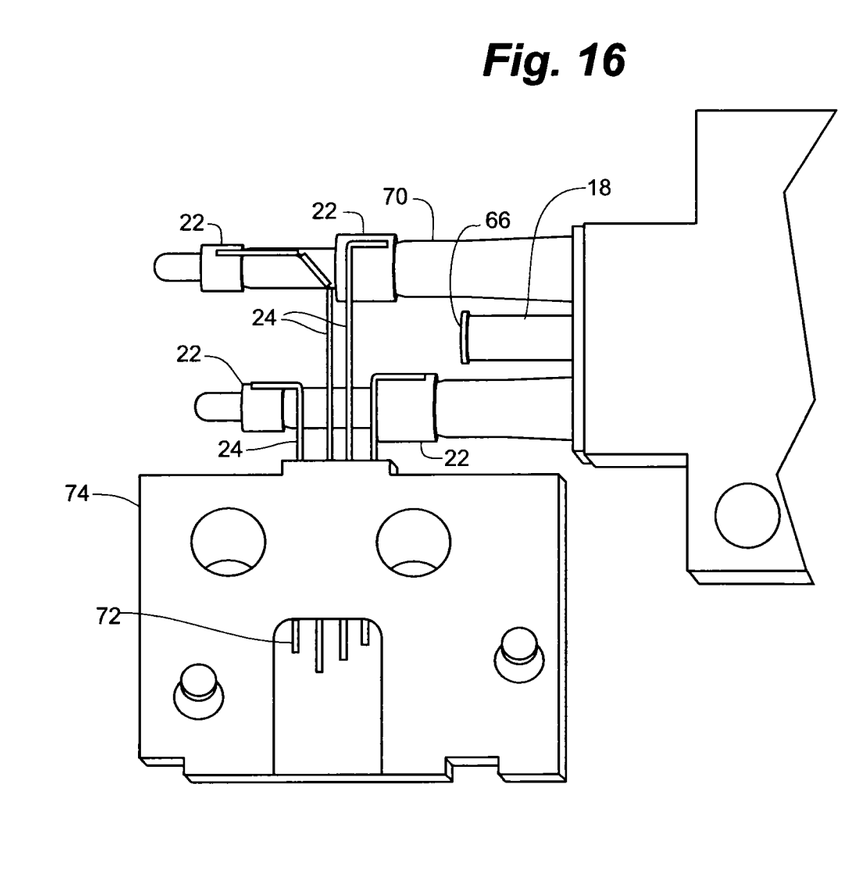
FIG. 16 is a perspective view of the partial set-up for injection molding a header.

Once the welds have been made, cross-holes that are located in the contact blocks 22 and rings of the welded sub-assemblies are assembled onto close tolerance core pins 70 as seen in FIG. 16. These core pins 70 are designed to satisfy both, the very strict standards of the medical device industry and effectively eliminate flash that can occur during the molding process. An acceptable shut-off region is thereby created around the interior diameter of all the contact blocks 22 and contact rings 48.

Next, the distal ends 72 of the conductor wires 24 are placed in shut off regions located adjacent to the mold cavity (placed in a loose cavity block 74). See FIG. 16. The shut-off region locations are critical in that they control the position of the wires 24 exiting the molded header 10 and must be in line with the mating wires on a corresponding medical device. Numerous wire locations and sizes are made possible that can be adapted to a variety of devices.

As seen in FIG. 16, the female threaded anchor 18 is placed onto a specially designed core pin that controls the exact position necessary for the alignment of the male mating threaded fastener used to lock in the lead.

Figure 17:
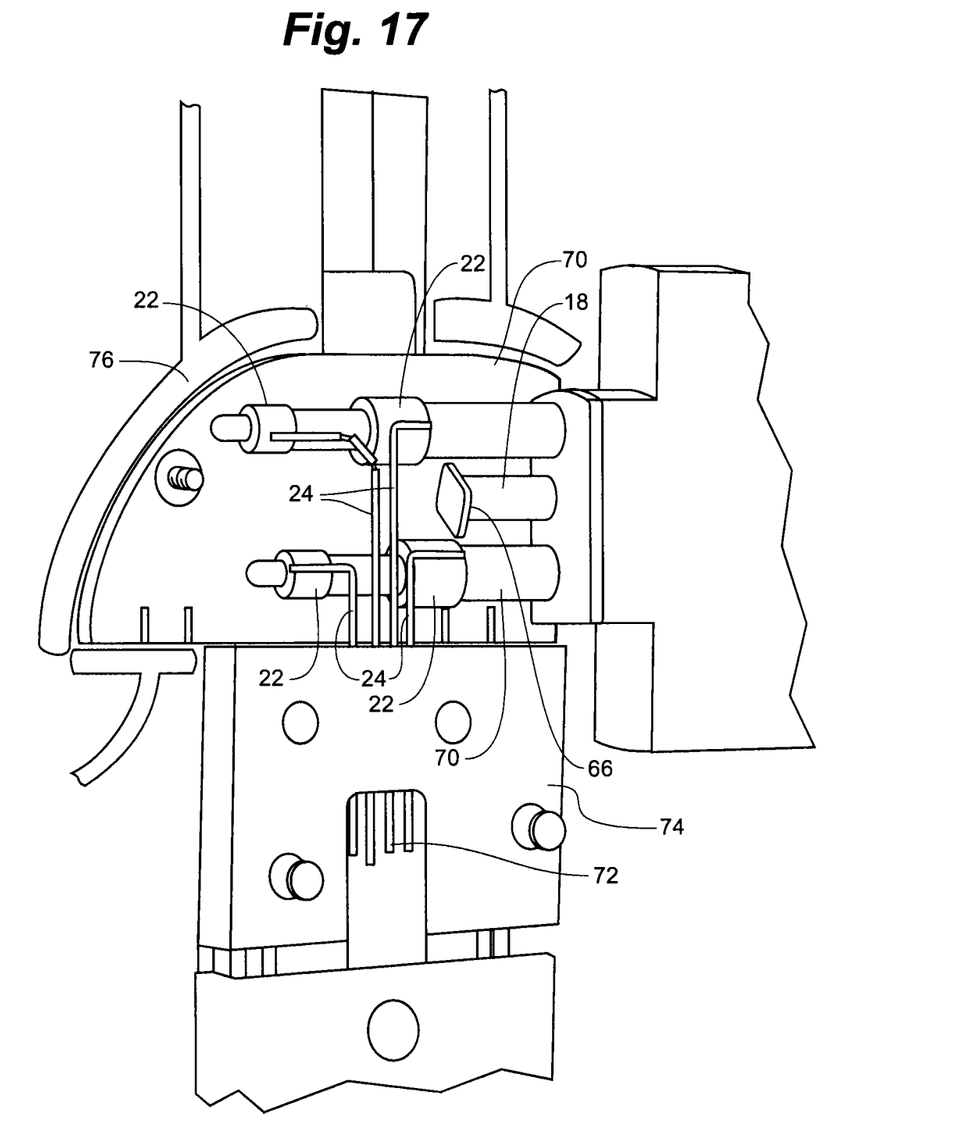
FIG. 17 is a perspective view of the set up for injection molding a header.

After all components have been properly seated on the core pins 70 and loose core block 74, the assembly is placed into the mold cavity 76 seen in FIG. 17 and is overmolded with a polymer. The typical polymer used for this application is a Thermoplastic Polyurethane, but is not limited to this specific polymer. During the injection molding process, extreme plastic injection pressures are necessary. Therefore, the welded subassemblies must withstand the stresses and plastic flow velocity that are created during the filling of the cavity. The mold design and sub-assembly configuration addresses potential issues such as the fatigue or breakage of weld joints, movement of wires 24 and maintaining the precise position of the contact blocks 22 and rings 48.

Once the injection molding and cooling process is complete the core pins 70 are extracted from the molded header housing 12. The molded header housing 12 is then ejected from the mold. At this phase, all the subassemblies and components are fully encapsulated with the polymer. The distal ends 72 of the wire conductors 24 are exposed for trimming to proper length (if necessary) which will facilitate the welding process during the connection phase to the medical device.

The fully encapsulated header is electrically tested as necessary to ensure proper resistance and voltage can be accomplished. Such a test demonstrates the robustness and reliability of this unique process wherein the weld joints and shut-off regions of all the conductive components are known to be reliable.

The final step in this manufacturing process is to attach the lead lock member 16. In general, the lead lock member 16 is simply attached with one or more fasteners 20 to the end of the molded header. The fasteners 20 are secured through the lead lock apparatus where it bottoms out against a step in the lead lock apparatus. The countersink (step) functions as a positive stop against the head of the fastener which gives the ability to "draw in" the lead lock system during fastening. The fastener 20 is secured to the molded-in female threaded anchor or anchors 18 which is precisely aligned with the fastener 20.

FIGS. 18-27 set forth an alternate embodiment of the header design of the present invention. This design provides a slightly different structure and manner in which leads can be locked in place and retained in a molded header device which encapsulates its interior conductive members. In this embodiment, a lock wing located in a recessed region of the header assembly is enabled to rotate upon manipulation to a locked configuration where its projecting features compress against the insulation of inserted leads and secure them in place. See FIGS. 24 and 25.

Figure 18:
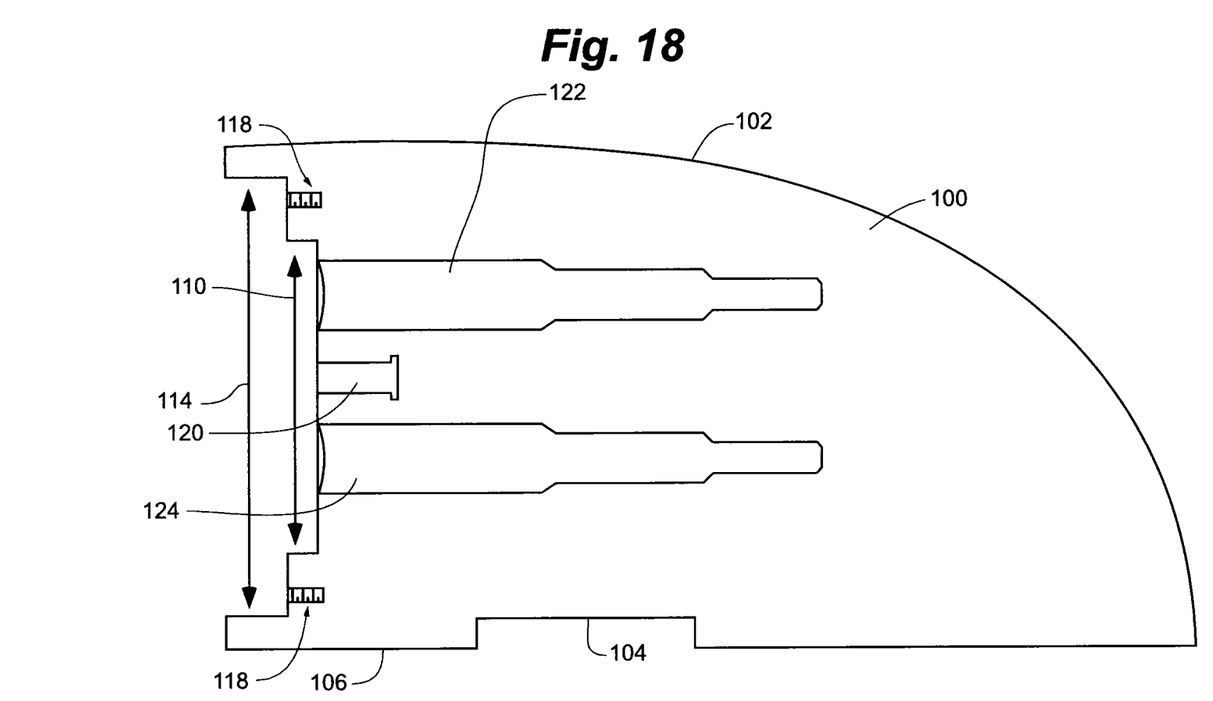
FIG. 18 is a cross-sectional view of the molded header housing for an alternative embodiment of a header.

FIG. 18 discloses the general overall shape of a molded polymer housing 100 utilized in this alternative embodiment. As in previously discussed embodiments, the housing is relatively thin and has a generally smooth outer surface with a rounded periphery spanning its top edge 102. The exact shape of the housing member 100 and its features are determined during the injection molding process. A bottom recessed pocket region 104 is located in the bottom face 106 of the device for welding wires from the header and main medical device together during assembly. The left side of the housing 100 of the device in FIG. 18 shows a two tiered recess for placement of the lead locking mechanism. The first inner recess 110 providing space for a lock wing 112 to be installed and the second outer recess 114 providing space for the lock wing retention plate 116 to be installed over the lock wing 112. Clearance exists for lock wing movement when both features are installed.

Two female threads 118 extend inward into the housing from the outer recess 114. These female threads 118 may be formed in the plastic of the housing 100 during molding formation using a threaded core pin. Alternatively, these threads 118 may be insert molded using a metal housing anchor with female threads formed in the interior of the housing 100. Molded-in threaded features of this type are precisely positioned using close toleranced positioning tooling. Two or more threaded positions may be possible depending upon the desired design.

An anchor 120 with female interior threads is part of the molded-in housing design as well. This anchor 120 is centrally positioned between the two lead bores 122 and 124 in FIG. 18. This threaded component aligns with and accepts a male threaded locking fastener of locking screw 150. This anchor 120 is also precisely located using close tolerance position tooling.

Contact blocks, rings, and wires are not set forth in FIG. 18, although the configuration of such conductive components in this design is similar to the one seen in FIG. 1 for the embodiment of FIGS. 18-27. In this embodiment, the contact blocks and rings are molded in around the perimeter of the bore members 122 and 124. These contact blocks are welded to conductor wires before the extrusion molding process takes place. The conductor wires are largely encapsulated in polymer material and exit the polymer housing into recessed pocket 104.

Figure 19:
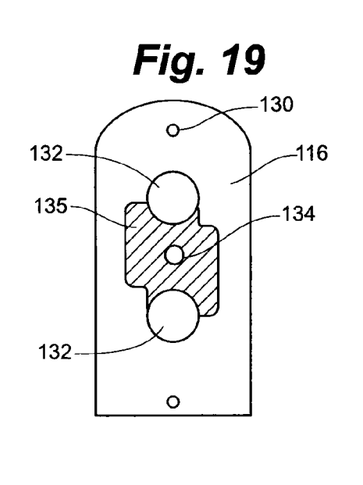
FIG. 19 is a cross-sectional end view of the retention plate of the header of FIG. 18.
Figure 20:
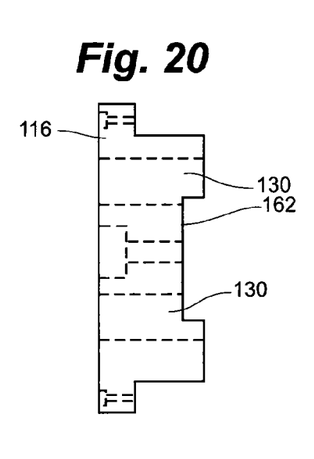
FIG. 20 is a cross-sectional side view of the retention plate of the header of FIG. 18.

The lock wing retention plate 116 is shown in FIGS. 19 and 20. The lock wing retention plate 116 is generally a member sized to fit within the outer recess 114 of the molded housing 100 so that the outer face of the retention plate 116 is generally flush with the edge of the housing 100. Further views of the retention plate 116 can be seen in greater detail in FIGS. 24 and 25. The retention plate 116 has a plurality of apertures 130 for fastener holes which correspond to the female threaded members 118 found within the polymer housing 100. The retention plate 116 also contains apertures 132 in corresponding axial alignment with the bore holes 122 and 124 present in the housing 100 when assembled. The retention plate 116 further includes a central screw hole 134 aligned with the axis of the bore of the anchor member 120.

As seen in FIG. 19, a recessed region 135 is found in the retention plate 116. This recess 135 is shaped for mechanical movement of a lock wing 112. Recessed portions are found between and partially adjacent to the bore holes apertures 132. The recess 135 being shaped such that it may act as a positive stop 137 for a lock wing 112 so that it cannot turn past ninety degrees.

Figure 21:
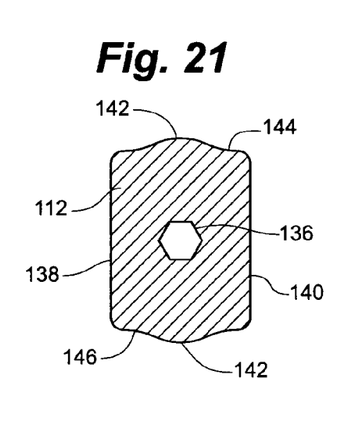
FIG. 21 is a side view of the lock wing of the header of FIG. 18.

FIG. 21 discloses the plastic wing lock 112 of the header design. The plastic wing lock 112 is a somewhat rectangular shaped nonconductive component having a central hex shaped aperture 136 and a perimeter which is relatively flat on two opposing sides 138 and 140 and which has outwardly projecting features 142 on the remaining pair of opposing sides 144 and 146. These outwardly projecting features 142 will be used for retaining lead members. All features of the wing lock 112 have generally smooth contours which serve to eliminate the risk of damage to the silicone shielding encapsulating the leads.

Figure 22:
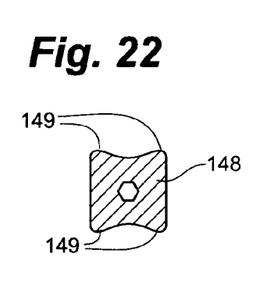
FIG. 22 is an alternate embodiment of the lock wing of FIG. 21.

A wide variety of designs can be used for the wing lock component 112 in addition to the shape shown in FIG. 21. One such alternative wing lock design 148 is shown in FIG. 22 where the protrusions 149 are located at the corners of the wing lock 148 rather than the center. The locking capabilities of this design is preferable in many instances.

Figure 23:
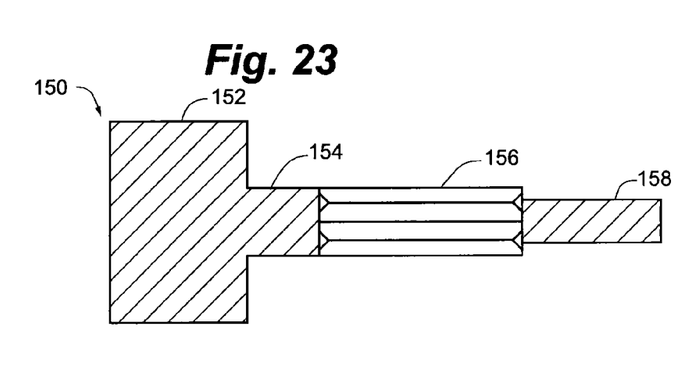
FIG. 23 is a cross-sectional view of a locking screw for the header of FIG. 18.
Figure 24:
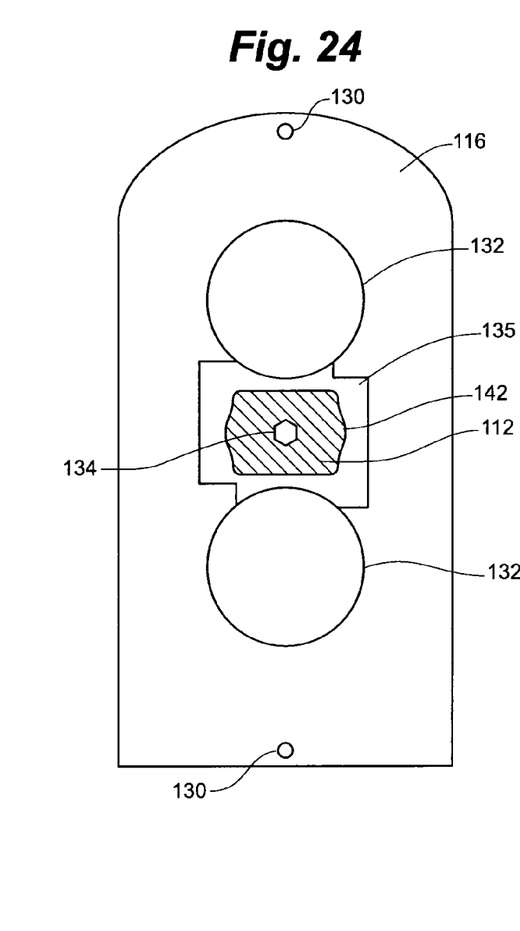
FIG. 24 is an end view of the header of FIG. 18 with the lock wing in the unlocked position.
Figure 25:
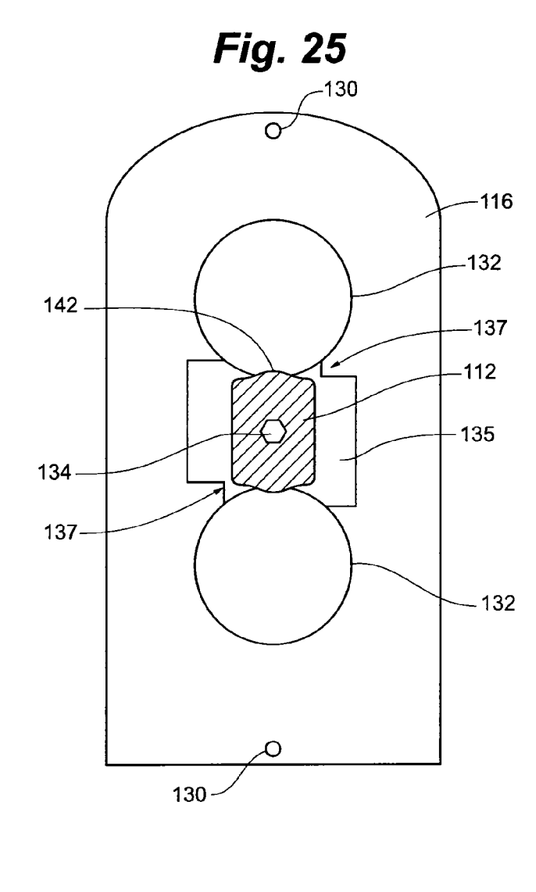
FIG. 25 is an end view of the header of FIG. 18 with the lock wing in the locked position.

A cross-section of the locking screw 150 for this header embodiment is shown in FIG. 23. The sections of this locking screw 150, from left to right, include a female hex head 152, a smooth shaft diameter portion 154, a male hex portion 156, and male threaded portions 158. When assembled, this locking screw 150 is placed through the retention plate 116 and the plastic lock wing 112. The male hex section 156 on the locking screw 150 aligns with the female central hex shaped hole 136 on the lock wing 116. The smooth shaft diameter 154 on the locking screw 150 aligns with the central screw hole 134 of the retention plate 116 allowing the screw 150 to turn without creating stress on the lock wing retention plate 116. Inside male threads of portion 158 of the locking screw 150 engage with the threads found in the anchor 120 molded into the header housing 100. The outer female hex head 152 of the locking screw 150 may be turned with a hex torque wrench from outside the header device. This is done to turn the lock wing 112 into position once leads have been inserted into the header.

The recessed region 135 of the retention plate 116 is designed to act as a positive stop. Therefore, when the locking screw 150 is turned in or out, the plastic lock wing 112 cannot turn past ninety degrees and allows the screw 150 to travel in or out. Accordingly, the locking screw 150 draws in the lock wing retention plate 116 into the recess in the polymer housing 100. Once the retention plate 116 is bottomed out against the raised portion of the retention plate and header, fasteners located above the main bores 122 and 124 are turned into the clearance holes 130 to hold the system in place.

What is formed by the recesses of both the retention plate 116 and the recesses of the header housing 100 is a small clearance pocket 162. In this clearance pocket 162 the plastic lock wing 112 may move to the locked position of FIG. 25 or the unlocked position of FIG. 26. The positive stops 137 formed by the recess 135 of the retention plate 116 limits the travel of the lock wing to ninety degrees of movement.

Therefore, a surgeon may secure leads within the header during surgery by first inserting the leads into bore holes 122 and 124 when the lock wing 112 is in the unlocked position. Next, the surgeon uses a hex wrench to turn the locking screw 150 such that the lock wing 112 rotates ninety degrees within the recessed portion 135 of the retention plate 116 to the locked position. The projecting members of the lock wing 112 compress against the silicone shielding encapsulating the lead to lock it in place. The compression points are outside of the sealing surfaces allowing for a fully functional lead without risk of bodily fluid leakage or other interference.

Figure 26:
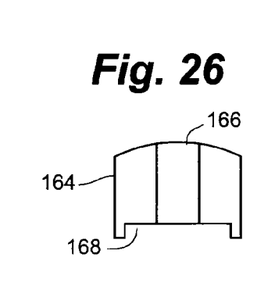
FIG. 26 is a cross-sectional view of the silicone septum plug of the header of FIG. 18.
Figure 27:
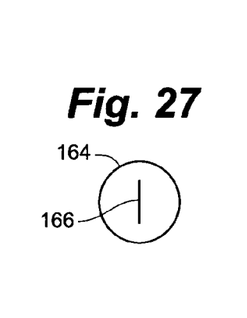
FIG. 27 is a top view of the silicone septum plug of the header of FIG. 18.

Finally, the silicone septum plug 164 seen in FIGS. 26 and 27 is used to cover the head of the hex locking screw 150 which is sealed into a counterbore. The septum plug 164 is designed to allow slight movement of the screw 150 during locking and unlocking the leads. The slit 166 in the silicone septum plug 164 is for the hex wrench and can be seen in the top view of FIG. 27 and the cross-section seen in FIG. 26. The recess 168 for screw movement can be seen in FIG. 26 as well.

This system may be used with one or more bores in a similar fashion to the embodiments discussed herein.

Therefore these embodiments of the present invention overcome problems in past header designs and provide a header design of increased reliability, safety, ease of use, and overall enhanced design.

The invention claimed is:

1. A method of manufacturing a header for an implantable medical device comprising:
   providing a plurality of header components including preformed wire conductors, contact blocks, contact rings, and a female threaded anchor for construction of a header housing assembly;
   assembling a header housing assembly by:
      welding ends of the preformed wire conductors to the contact blocks and the contact rings to form sub-assemblies;
      positioning the contact blocks and the contact rings of the welded sub-assemblies onto core pins;
      placing distal ends of the preformed wire conductors in shut off regions adjacent a mold cavity;
      coupling the female threaded anchor with a further core pin;
   placing the header housing assembly into the mold cavity;
   overmolding the header housing assembly with a polymer;
   extracting the core pins and further core pin from the mold cavity;
   ejecting the header housing assembly from the mold cavity;
   testing the header housing assembly electrically; and
   attaching a lead lock member to the header housing assembly.

2. The method of manufacturing a header for an implantable medical device of claim 1 wherein the welding step comprises resistance welding or laser welding.

3. The method of manufacturing a header for an implantable medical device of claim 1 wherein:
   the header housing assembly comprises:
      a recessed portion, a plurality of bores sized to receive leads and provide lead access to one or more of the wire conductors; and
      the lead lock member is attached in the recessed portion of the header housing assembly and includes a plurality of apertures with inwardly-tapering collet members disposed about the apertures, and a lock screw engageable within the female threaded anchor to cause axial constriction of the collet members within the bores to lock in place leads inserted into the bores.

4. The method of manufacturing a header for an implantable medical device of claim 3 wherein the lead lock member is attached entirely within the header housing assembly when locked in place except for an exposed face of the lead lock member allowing for lead access.

5. The method of manufacturing a header for an implantable medical device of claim 3 wherein the collet members do not extend beyond a first diameter region of the bores such that seals formed by the collet members are located in the first diameter region of the bores.

6. The method of manufacturing a header for an implantable medical device of claim 3 wherein the lock screw cannot be completely detached from the lead lock member.

7. The method of manufacturing a header for an implantable medical device of claim 3 wherein the header housing assembly has two bores for receiving leads.

8. The method of manufacturing a header for an implantable medical device of claim 3 wherein the header housing assembly contains a bottom recess pocket for wire access.

9. The method of manufacturing a header for an implantable medical device of claim 3 wherein the tapered collet members have inwardly projecting flanges.

10. The method of manufacturing a header for an implantable medical device of claim 3 wherein the bores and the female threaded anchor have axes of similar orientation such that leads and the lock screw can be manipulated by a physician from a similar orientation.

11. The method of manufacturing a header for an implantable medical device of claim 3 wherein the lead lock member is concealed in the header housing assembly.

12. The method of manufacturing a header for an implantable medical device of claim 1 wherein:
the header housing assembly defines a plurality of lead bores molded within the header housing assembly for receiving leads wherein each of said lead bores includes an electrical contact at the bore perimeter coupled to a wire; and
the lead lock member defines a plurality of apertures surrounded by collet member protrusions for alignment with said plurality of lead bores, and includes a fastener that engages the female threaded anchor and is adjustable to cause constriction of the lead lock member upon engagement of the fastener;
wherein the axes of the apertures are offset from the axis of the fastener.

13. The method of manufacturing a header for an implantable medical device of claim 12 wherein the lead lock member is located completely within a recess of the header housing assembly when fully engaged such that only one face of the lead lock member is exposed.

14. The method of manufacturing a header for an implantable medical device of claim 13 wherein the collet member protrusions only extend into a first large diameter region of the lead bores so that seals formed by the collet member protrusions are located in the first diameter region of the bores.

15. The method of manufacturing a header for an implantable medical device of claim 13 wherein the header housing assembly has two lead bores.

16. The method of manufacturing a header for an implantable medical device of claim 13 wherein the bores and the female threaded anchor have parallel axes such that leads are inserted and the fastener is manipulated from a similar orientation.

17. The method of manufacturing a header for an implantable medical device of claim 13 wherein the lead lock member is machined.

18. The method of manufacturing a header for an implantable medical device of claim 1 wherein:
the header housing assembly includes a plurality of bores sized to receive leads and provide lead access to one or more of the wire conductors, a two-tiered recessed region having an inner recess and an outer recess, and a plurality of threaded features, and an internally threaded anchor; and
the header housing assembly includes:
a lock wing located within the inner recess of the header housing assembly containing a plurality of outwardly projecting features on at least two locations for interfering with leads received in the bores;
a lock wing retention plate secured within the outer recess of the header housing, the lock wing retention plate having a recess region shaped to accommodate rotational movement of the lock wing between a locked position and an unlocked position, and a plurality of apertures aligned with the bore leads, and threaded features of the header housing assembly;
a plurality of threaded locking fasteners to secure the lock wing retention plate to the housing; and
a locking screw for rotating the lock wing between the locked position and the unlocked position.

19. A method of manufacturing a header for an implantable medical device comprising:
providing a plurality of header components including preformed conductive components, contact blocks, contact rings, and a threaded anchor for construction of a header housing;
assembling a header housing assembly by:
welding ends of the preformed conductive components to contact blocks and contact rings to form sub-assemblies;
positioning the contact blocks and the contact rings of the welded sub-assemblies onto core pins;
placing distal ends of the preformed conductive components in shut off regions adjacent a mold cavity;
coupling the threaded anchor with a further core pin;
placing the components and core pins of the header housing assembly into the mold cavity;
overmolding the header housing assembly with a polymer;
extracting the core pins and further core pin from the mold cavity;
ejecting the header housing from the mold cavity;
testing the header housing electrically; and
attaching a lead lock member to the header housing.

20. The method of manufacturing a header for an implantable medical device of claim 19 wherein:
the header housing comprises:
a recessed portion, a plurality of bores sized to receive leads and provide lead access to one or more of the preformed conductive components; and
the lead lock member is attached in the recessed portion of the header housing and includes a plurality of apertures with inwardly-tapering collet members disposed about the apertures, and a lock screw engageable within the threaded anchor to cause axial constriction of the collet members within the bores to lock in place leads inserted into the bores.

* * * * *